United States Patent [19]

Turpin et al.

[11] Patent Number: 5,110,319
[45] Date of Patent: May 5, 1992

[54] PROCESS FOR EXTRACTING ETHANOL FROM FERMENTATION BROTHS FOR DIRECT BLENDING INTO GASOLINE WHILE PRESERVING THE BROTH FOR RECYCLING

[75] Inventors: Jim L. Turpin, Fayetteville, Ark.; Robert B. Eldridge, Bartlesville, Okla.; Sharon Booth-McGee, Baton Rouge, La.

[73] Assignee: The Board of Trustees of the University of Little Rock Arkansas, Little Rock, Ark.

[21] Appl. No.: 537,131

[22] Filed: Jun. 13, 1990

[51] Int. Cl.$^5$ .............................................. C10L 1/02
[52] U.S. Cl. ..................................... 44/451; 203/44; 435/161; 568/913
[58] Field of Search .............. 44/53, 56, 451; 203/44; 435/161; 568/913

[56] References Cited

U.S. PATENT DOCUMENTS

| | | | |
|---|---|---|---|
| 2,182,550 | 12/1939 | Christensen | 44/53 |
| 4,251,231 | 2/1981 | Baird | 44/56 |
| 4,297,172 | 10/1981 | Kyle | 44/53 |
| 4,402,792 | 9/1983 | Horst | 44/53 |
| 4,425,137 | 1/1984 | Roth | 44/53 |
| 4,441,891 | 4/1984 | Roth | 44/53 |
| 4,517,298 | 5/1985 | Tedder | 44/53 |

OTHER PUBLICATIONS

D. Tedder, "Continuous Fermentation and Product Recovery by Liquid-Liquid Extraction", Biotech 84 USA pp. A177–A188.

Minier and Goma, "Ethanol Production by Extractive Fermentation" Biotechnology and Bioengineering, vol. XXIV, pp. 1565–1579 (1982).

Crabbe et al., "Effective Microorganisms on Rate of Liquid Extraction of Ethanol From Fermentation Broths", Biotechnology and Bioengineering, vol. XXVIII, pp. 939–943. (1986).

Kollerup and Daugulis, "Screening and Identification of Extractive Fermentative Solvents Using a Data Base", Can. J. Chem. Eng. (63) 919 (1985).

Primary Examiner—Margaret B. Medley
Attorney, Agent, or Firm—Hermann Invester

[57] ABSTRACT

A method of producing ethanol from a fermentation source for direct blending into gasoline to form gasohol is provided by extracting ethanol from the fermentation broth with a non-toxic solvent compatible with gasoline. The invention includes extraction outside of the fermentor and the recycling of the extracted broth back to the fermentor. An extracting column is used for the extraction and recycling and the extract can be dried before blending it with the gasoline. The preferred solvent is an alkylate.

11 Claims, 1 Drawing Sheet

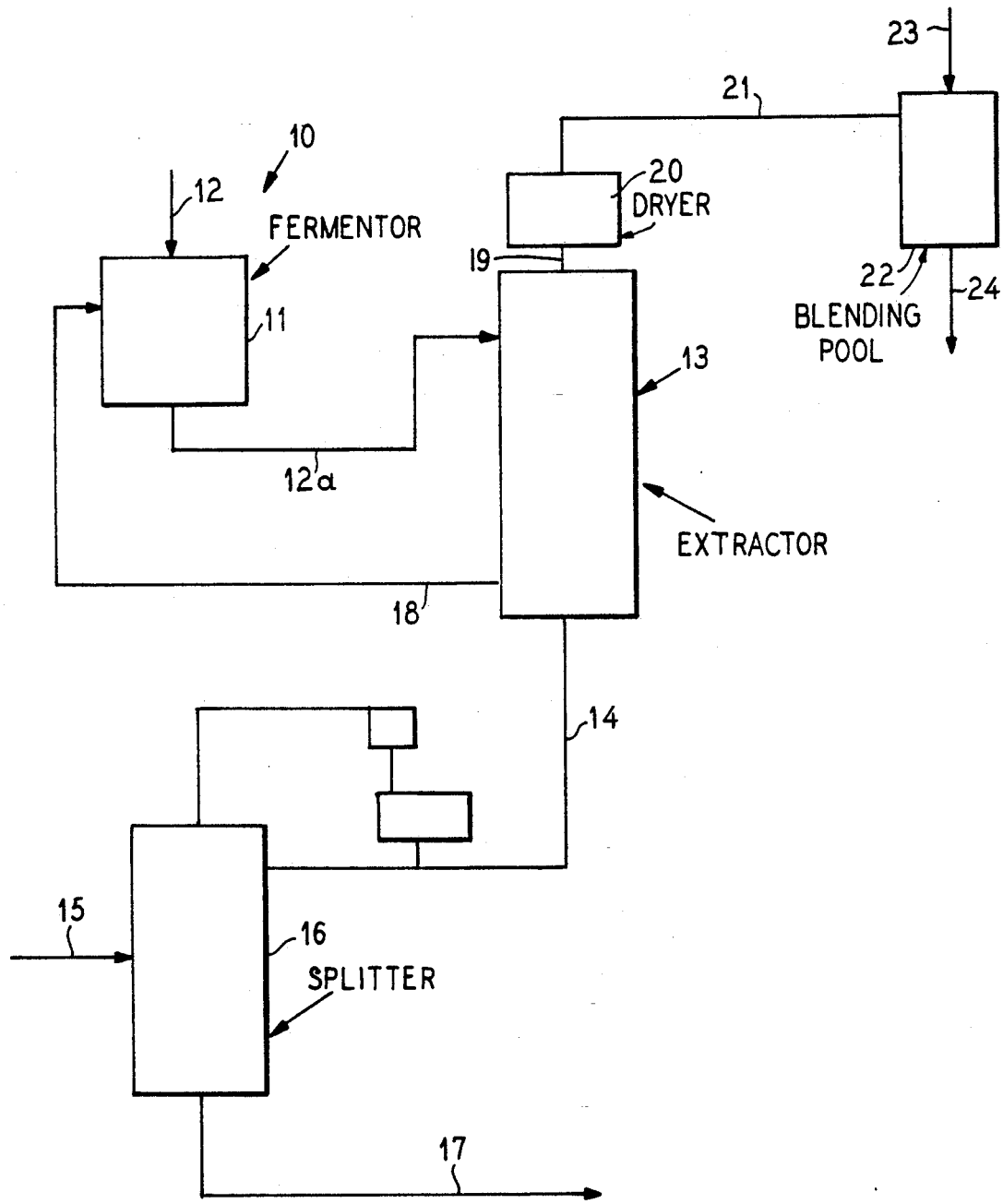

PROCESS FOR EXTRACTING ETHANOL FROM FERMENTATION BROTHS FOR DIRECT BLENDING INTO GASOLINE WHILE PRESERVING THE BROTH FOR RECYCLING

BACKGROUND OF THE INVENTION

The invention relates to the art of extracting ethanol from a fermentation broth while preserving the broth for reuse and accommodating direct blending of the ethanol extract into gasoline. Specifically, the invention deals with the extraction of ethanol from a fermentation broth with a non-toxic solvent compatible with gasoline to form "Gasohol", removing the extract, and recycling the broth for continued fermentation.

DESCRIPTION OF THE PRIOR ART

Heretofore, as exemplified by Baird U.S. Pat. No. 4,251,231 issued Feb. 17, 1981, gasoline has been used as a solvent for the direct extraction of ethanol from a fermentation broth. A major drawback of this process is that the gasoline is toxic to the ethanol-producing microorganisms and the broth has to be discarded. The carbon source and all of the remaining nutrients in the broth are lost. A batch procedure is required which decreases the efficiency and production rate of the process.

An article by D. Tedder et al entitled "Continuous Fermentation and Product Recovery By Liquid-Liquid Extraction" proceedings of Biotech 84 U.S.A. pages A 177–A188 suggests that a blend of tri-n-butyl phosphate and "Isopar-M" ® solvent is useful in maintaining a reduced ethanol concentration in a fermentor. The co-solvent mixture was found to be bio compatible with the fermentation yeast and the ethanol was removed from the solvent by evaporation permitting the ethanol freed solvent to be recycled back to the extractor. The solvent was separated from the ethanol and recycled. The extract was not suitable for direct blending into a gasoline.

Prior known bio extraction schemes contacted the fermentation broth and the solvent inside the fermentation vessel. An article by Minier and Goma entitled "Ethanol Production By Extractive Fermentation", Biotechnology and Bioengineering Vol. XXIV, pages 1565–1579 (1982) describes extracting ethanol in an immobilized cell column containing saccharomyces cerevisiae yeast with 1-dodecanol as a solvent. The extraction was effected inside the fermentation vessel.

An article by Crabbe et al entitled "Effective Microorganisms On Rate of Liquid Extraction of Ethanol From Fermentation Broths", Biotechnology and Bioengineering Vol. XXVIII, pages 939–943 (1986) discloses that the presence of microorganisms in the aqueous phase of the extraction reduces the rate of extraction.

An article by Kollerup and Daugulus entitled: "Screening and Identification of Extractive Fermentative Solvents Using a Data Base" Can. J. Chem. Eng. (63) 919 (1985) reports the screening of solvents non-toxic to microorganisms and reports that only a few are non-toxic to the fermentative yeast "saccharomyces cerevisiae".

While these prior disclosed bioextraction schemes recognize that toxicity of the solvent on the fermentation broth could be reduced by solvents other than gasoline, they did not provide anything that could be worked into a continuous fermentation process of producing ethanol, extracting the ethanol from the fermentation broth by a non-toxic solvent outside of the fermentor forming an extract directly blendable into gasoline, and recycling the extract freed broth back to the fermentor.

It would therefore be a definite improvement in this art to provide a fermentation process of producing ethanol for direct blending into gasoline stock without damaging the fermentation broth.

It would be an additional improvement in this art to extract ethanol from a fermentation broth with an alkylate outside of the fermentor and to recycle the broth for reuse in the fermentor.

SUMMARY OF THE INVENTION

According to this invention, ethanol is produced in a fermentor from conventional fermentation broths containing a carbon source, such as glucose, and fermentation microorganisms such as yeasts. Saccharomyces cerevisiae is a preferred yeast. The ethanol containing broth is discharged from the fermentor and run through an extraction column in counter-flow relation with a non-toxic solvent compatible with gasoline, preferably an alkylate. The extract containing about 8–10% ethanol is directly blended into standard gasoline stocks to produce fuels generally referred to as "gasohol". The extract freed broth is recycled back to the fermentor with its remaining carbon source and nutrients preserved for continued fermentation.

The process thus provides a very cost effective method of producing "gasohol" and combined alkylate extraction of ethanol with a recycle procedure. Flow rates are set to maintain a constant ethanol concentration in the fermentor to avoid high concentrations of ethanol which inhibit the microorganism productivity in the fermentor. A constant purging of alcohol from the fermentor also favorably affects the rate of ethanol production. The process yields an alkylate stream containing ethanol and water and, after desirable dehydration, this stream can be blended directly into the gasoline mix pool thus introducing both high octane and oxygenated components into the "gasohol".

The invention will be further understood from the attached sheet of drawing which illustrates a method of this invention.

DETAILED DESCRIPTION OF THE PREFERRED EMBODIMENTS

In a preferred embodiment of the present invention, Saccharomyces cerevisiae is used as the yeast in the fermentor since it is relatively resistant to contamination and withstands extremes in pH. This tolerance eliminates contaminating microorganisms from the fermentation broth and this type of yeast is easily and quickly cultured. In the preferred embodiment of the present invention, the extracting solvent is an alkylate. It is substantially free from impurities, and has a boiling range of 50°–150° C.

In the preferred embodiment of this invention, ethanol concentrations in the fermentor are kept well below 12%—preferably around 6–8% to avoid inhibition of the yeast and for this purpose, the ethanol containing broth is continuously removed from the fermentor to maintain a low ethanol concentration in the fermentor.

As illustrated in the attached drawing, apparatus 10 for carrying out the process includes a standard fermentor 11 receiving fermentation broth including a carbon source and microorganisms at 12 which are agitated and maintained at a desired fermentation temperature as is conventional in the production of ethanol from nutrient broths and microorganisms. The broth is preferably a water solution of glucose and yeast such as Saccharomyces cerevisiae. The fermentation in the fermentor 10 is maintained to produce an ethanol content substantially below 12% by volume and preferably in the range of about 6–8%.

The ethanol containing broth is drained through a first stream 12a discharging into the upper end of an extraction column 13 where it flows downwardly through the extractor. A second stream 14 releases a light alkylate into the bottom of the column 13 for upward countercurrent flow relative to the downward flow of the broth. The light alkylate is fed from an alkylate source stream 15, separated in a splitter 16 with the light end boiling in the range of 50°–150° C. pumped to the stream 14 and the heavy end discharged at 17.

The extracted broth freed from the ethanol is recycled through a stream 18 back to the fermentor where its remaining nutrients and microorganisms are utilized to enrich the feed stream 12.

The ethanol containing alkylate extract is discharged through a stream 19 at the top of the extractor to flow through a dryer 20, such as a desiccator, to remove any excess water content. The ethanol content in the stream 19 is about 8% by weight.

The dry extract or alkylate stream discharges from the dryer 20 through a stream 21 to a blending pool 22 fed from a gasoline stream 23 to produce "gasohol" of about an 8% ethanol content which is discharged at 24.

A typical fermentor includes a liquid feed reservoir, a pump, a light source, a liquid flow breaker, an agitator, a gas sparger, a liquid level control, and a product reservoir from which the broth is drained and recycled.

In a specific run, the initial starting batch of the glucose water solution having a glucose concentration of 100 grams per liter was inoculated to provide a starting cell concentration of about 1 gram per liter using a yeast extract concentration of 3 grams per liter. The pH of the broth was lowered to 4.0 with one normal hydrochloric acid to deter contamination. The broth was agitated at a speed of 100 R.P.M. and the temperature was maintained at 30° C.

The fermentation was continued until the ethanol concentration was approximately 35 grams per liter, at which time the stream 12a was opened to the extraction column 13. The broth was then recycled back to the fermentor 11, and a concentrated solution of glucose and yeast extract was added to the fermentor to restore the glucose concentration to 100 grams per liter. The fermentation was continued to maintain a desired ethanol concentration for feeding to the extractor.

The extraction was carried out at a steady state with a solvent feed ratio ranging from 5–20 by volume and the solvent was disbursed through the column at a rate of 200–450 milliliters per minute. The continuous phase rate ranged from 20–50 milliliters per minute.

The blending in the gasoline pool was regulated to provide "gasohols" of desired ethanol contents such as 6–10% by weight.

From the above descriptions, it should be understood by those skilled in this art that this invention makes possible the direct blending of solvent extracted ethanol from a fermentor into a gasoline pool to produce gasohol while maintaining the fermentation broth with its remaining nutrients and carbon source for recycling back to the fermentor.

We claim as our invention:

1. A method of producing gasohol which comprises fermenting ethanol-producing source material in a fermentor, releasing fermentation broth from the fermentor into an extractor, releasing a light alkylate having a boiling range of 50°–150° C. into the extractor for countercurrent flow relative to the fermentation broth, flowing the extract from the extractor, blending gasoline with the extract to provide a desired ethanol content in the gasoline, and recycling the extract freed fermentation broth back to the fermentor.

2. The method of effeciently and continuously producing ethanol from a fermentation source for direct blending into gasoline which comprises fermenting a fermentation broth to a desired ethanol concentration, circulating the ethanol containing broth through an extractor, feeding an alkylate having a boiling range of 50°–150° C. which is not toxic to the broth and is blendable with gasoline through the extractor for solvent extraction of the ethanol from the broth and adding the solvent freed broth to fresh fermentation broth for augmenting the nutrient content thereof.

3. In a continuous method of producing ethanol from a fermentation broth, the steps of effecting the fermentation with Saccharomyces cerevisiae, extracting ethanol from the fermented broth with a light alkylate having a boiling range of 50°–150° C. which is not toxic to the broth and is compatible with gasoline, and recycling the ethanol freed broth back to the fermentation broth.

4. The method of claim 1, wherein the fermentation and recycling of the extract freed broth are continuous to maintain an ethanol concentration of less than 12%.

5. The method of claim 1, including the added step of drying the extract prior to the blending step.

6. The method of claim 1, wherein the fermentation broth is a water solution of glucose and a yeast.

7. The method of claim 6, wherein the yeast is Saccharomyces cerevisiae.

8. The method of claim 2, wherein the alkylate is a saturated paraffin of highly branched molecular structures free from impurities with a boiling range of approximately of 50°–150° C.

9. The method of claim 2, wherein the fermentation is maintained at temperatures of about 30° C.

10. The method of claim 2, including the step of blending the extract with gasoline to provide an ethanol content in the gasoline of about 6–10%.

11. In the method of claim 3, the added step of removing water from the extract and blending the dried extract into a gasoline pool for producing gasohol.

* * * * *